(12) United States Patent
Jörgensen

(10) Patent No.: US 8,196,903 B2
(45) Date of Patent: Jun. 12, 2012

(54) AROMATIC NEBULIZING DIFFUSER

(75) Inventor: Carsten Jörgensen, Kastanienbaum (CH)

(73) Assignee: Ming Jen Hsiao, Miaoli County (TW)

( * ) Notice: Subject to any disclaimer, the term of this patent is extended or adjusted under 35 U.S.C. 154(b) by 469 days.

(21) Appl. No.: 12/574,752

(22) Filed: Oct. 7, 2009

(65) Prior Publication Data

US 2011/0079660 A1    Apr. 7, 2011

(51) Int. Cl.
*B01F 3/04* (2006.01)
(52) U.S. Cl. ............... 261/30; 261/78.2; 261/DIG. 88; 422/124; 239/102.1; 239/102.2; 239/144
(58) Field of Classification Search ............... 261/30, 261/78.2, DIG. 88; 422/124; 239/102.1, 239/102.2, 144
See application file for complete search history.

(56) References Cited

U.S. PATENT DOCUMENTS 3,970,250 A * 7/1976 Drews .................. 239/102.2

* cited by examiner

*Primary Examiner* — Robert A Hopkins
(74) *Attorney, Agent, or Firm* — Ming Chow; Sinorica, LLC

(57) ABSTRACT

An aromatic nebulizing diffuser includes a base panel (10), a power adapter (20), an electric fan (30), a shell (40), a fluid container (50), an oscillator (60) and a top over (70). The oscillator (60) oscillates an aromatic fluid in the fluid container (50) to produce a fine mist. The fluid container (50) has an air conduit (53) that reduces in direction from its bottom air inlet (531) toward its top air outlet (532) for causing acceleration of the speed of the induced flow of air to carrying the fine mist of aromatic fluid droplets out of jet holes (71) on the top cover (70). The fluid container (50) is detachably fastened to the base panel (10) by means of plugging bottom mounting rods (512) of the fluid container (50) into respective tubular upright posts (12) of the base panel (10), facilitating cleaning.

9 Claims, 5 Drawing Sheets

AROMATIC NEBULIZING DIFFUSER

BACKGROUND OF THE INVENTION

1. Field of the Invention

The present invention relates to an aromatic diffuser and more particularly, to such a nebulizing diffuser, which utilizes oscillation waves to atomize an aromatic fluid.

2. Description of the Related Art

Regular aromatic nebulizing diffusers or essential oil diffusers commonly have one single outlet for guiding out the generated fine mist of aroma or essential oil droplets. However, diffused water droplets may impact one another in the outlet, and a big ratio of the generated mist will be condensed into fluid that will flow back to the inside of the fluid container, lowering the nebulizing diffusion effect.

Further, in the fluid container of a conventional aromatic nebulizing diffuser or essential oil diffuser, a planar baffle is mounted on the inside to prohibit upward moving of the oscillated aromatic fluid or essential oil. However, this planar baffle causes the major part of the oscillated flow of aromatic fluid or essential oil to flow horizontally, hindering lift of the produced fine mist of aromatic fluid or essential oil droplets.

According to conventional designs, a person can simply see the lifting of the produced fine mist of aromatic fluid or essential oil from the outlet of the fluid container. The conventional designs cannot provide a visual lighting effect to illuminate the lifting of produced fine mist of aromatic fluid or essential oil in the dark or at night.

Further, when the aromatic fluid or essential oil in an aromatic nebulizing diffuser or essential oil diffuser is been oscillated to produce a fine mist of aromatic fluid or essential oil droplets, the wall of the aromatic nebulizing diffuser or essential oil diffuser tends be contaminated with aromatic fluid stains or essential oil stains. In this case, the aromatic nebulizing diffuser or essential oil diffuser must be cleaned so as not to lower the nebulizing performance. However, it is inconvenient to assemble and disassemble conventional aromatic nebulizing diffusers or essential oil diffusers, i.e., conventional designs do not facilitate cleaning.

Further, the single outlet design of conventional aromatic nebulizing diffusers or essential oil diffusers limits the variation of lifting mode of produced fine mist of aromatic fluid or essential oil droplets.

SUMMARY OF THE INVENTION

The present invention has been accomplished under the circumstances in view. It is main object of the present invention to provide an aromatic nebulizing diffuser, which has multiple holes for guiding out the generated fine mist of aromatic fluid droplets, facilitating atomization of the aromatic fluid and lifting of the generated fine mist of aromatic fluid droplets and avoiding condensing of the generated fine mist of aromatic fluid droplets, It is another object of the present invention to provide an aromatic nebulizing diffuser, which prevents splashing of the aromatic fluid during oscillation and has better performance in atomization of the aromatic fluid without increasing the capacity and oscillation frequency of the oscillator.

It is still another object of the present invention to provide an aromatic nebulizing diffuser, which can be easily assembled and disassembled, facilitating cleaning.

It is still another object of the present invention to provide an aromatic nebulizing diffuser, which provides lighting and visual effects, enabling people to see the variation of the lifting of the generated fine mist of aromatic fluid droplets.

It is still another object of the present invention to provide an aromatic nebulizing diffuser, which provides better atomization.

To achieve this and other objects of the present invention, an aromatic nebulizing diffuser comprises a base panel having a plurality of air vents cut through top and bottom sides thereof, an electric fan mounted on the base panel corresponding the air vents for drawing in air, a fluid container, which comprises a horizontal bottom wall, a mounting through hole cut through the horizontal bottom wall; a vertical peripheral wall upwardly extended from the border of the horizontal bottom wall, a fluid chamber surrounded by the horizontal bottom wall and the vertical peripheral wall and holding an aromatic fluid, an air conduit suspending in the fluid chamber, the air conduit having a bottom air inlet extending out of the horizontal bottom wall for guiding in currents of air from the electric fan and a top air outlet for suspending above the fluid level of the aromatic fluid, an ultrasonic oscillator mounted in the mounting through hole of the fluid container and controllable to produce oscillating waves for causing atomization of the aromatic fluid, a power adapter mounted on the base panel and electrically connected with the electric fan and the ultrasonic oscillator to provide the electric fan and the ultrasonic oscillator with the necessary working voltage, a shell surrounding the fluid container and having a top open side connected with the fluid container and a bottom open side connected with the base panel, and a top cover covered on the shell to close the fluid container, The top cover comprises a plurality of jet holes cut through top and bottom walls thereof in communication with the inside space of the fluid chamber and arranged in a circle, and an annular bottom flange protruded from the bottom wall and suspending in the top side inside the fluid chamber of the fluid container for baffling water.

The aromatic nebulizing diffuser further comprises a water lever sensor and a light source carried on the ultrasonic oscillator. The water level sensor is adapted to detect the level of the aromatic fluid in the fluid chamber. The light source is controllable by the ultrasonic oscillator to emit light in illuminating the fluid chamber.

Further, the shell can be prepared from a transparent or translucent that admits light.

DETAILED DESCRIPTION OF THE PREFERRED EMBODIMENT

Figure 1:
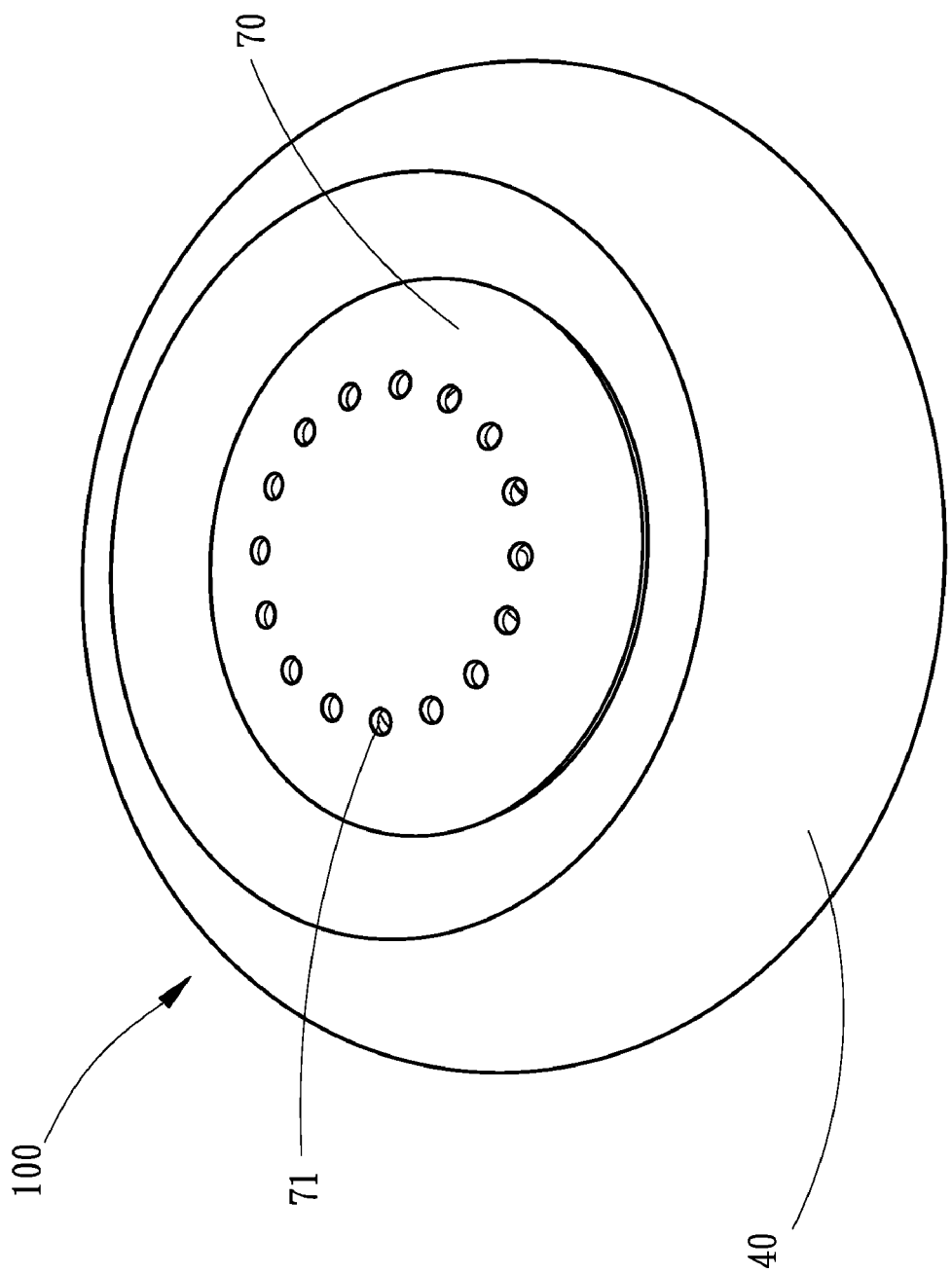
FIG. 1 is an oblique elevation of an aromatic nebulizing diffuser in accordance with the present invention.
Figure 2:
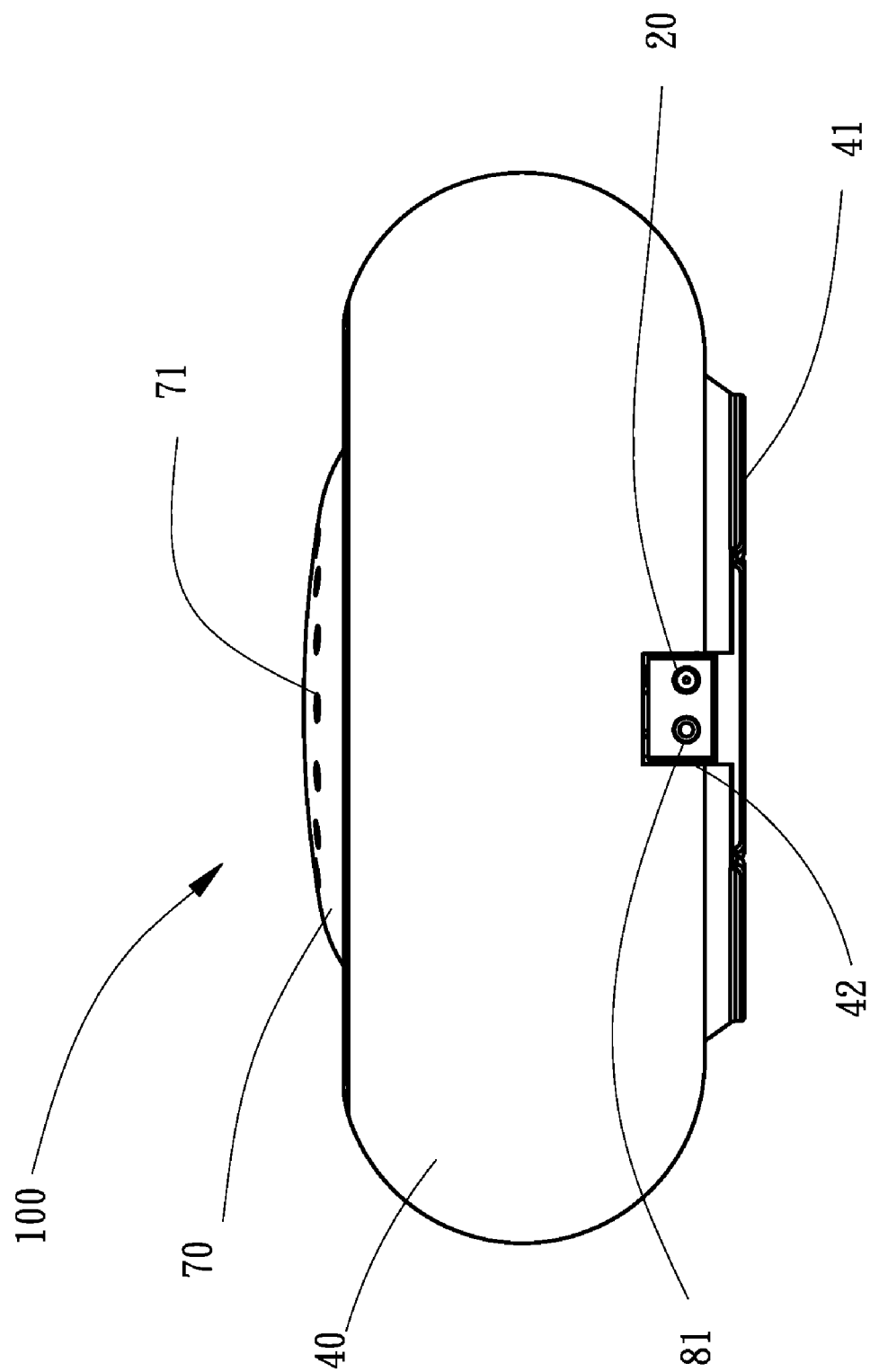
FIG. 2 is a sectional side view of the aromatic nebulizing diffuser in accordance with the present invention.
Figure 3:
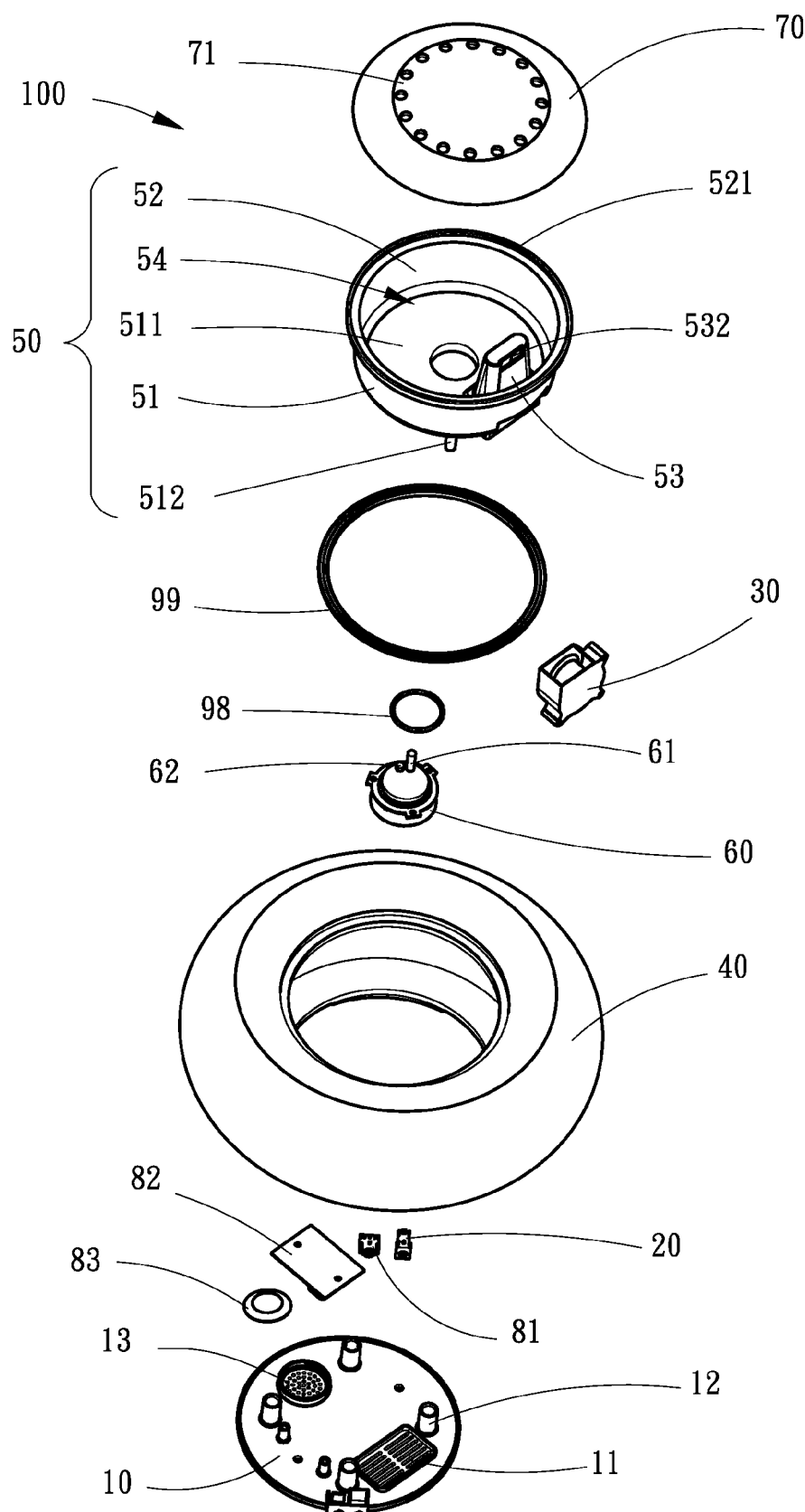
FIG. 3 is an exploded view of the aromatic nebulizing diffuser in accordance with the present invention.

Referring to FIGS. 1, 2 and 3, an aromatic nebulizing diffuser 100 in accordance with the present invention is shown comprising a base panel 10, a power adapter 20, an electric fan 30, a shell 40, a fluid container 50, and oscillator 60 and a top over 70.

Figure 4:
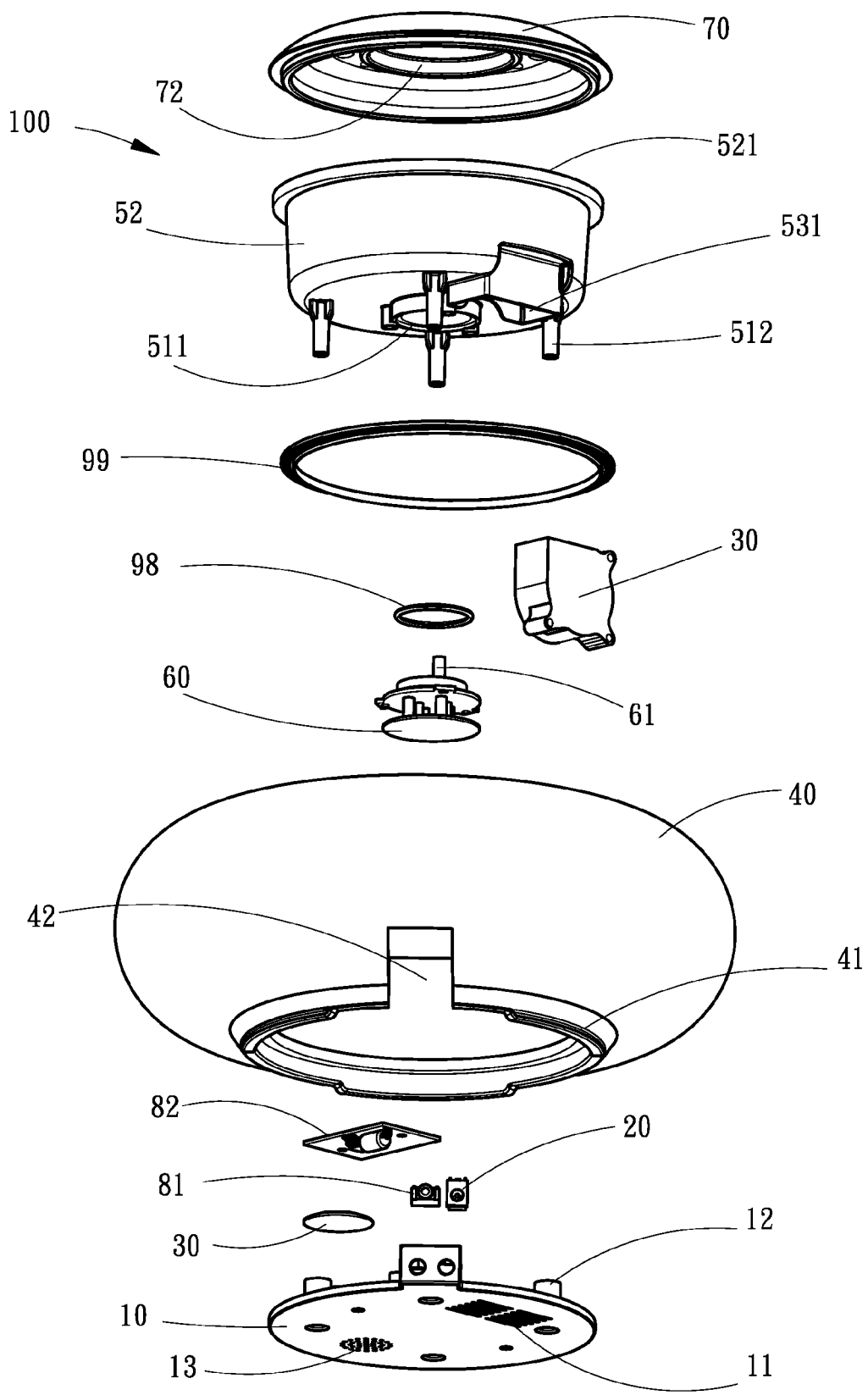
FIG. 4 is an exploded view of the aromatic nebulizing diffuser shown in FIG. 1 when viewed from another angle.

Referring to FIG. 4 and FIG. 3 again, the base panel 10 has a plurality of air vents 11 through which the electric fan 30 draw in air.

Referring to FIGS. 2 and 3 again, the power adapter 20 is mounted on the base panel 10 for the connection of an external power cable (not shown) for power input.

Figure 5:
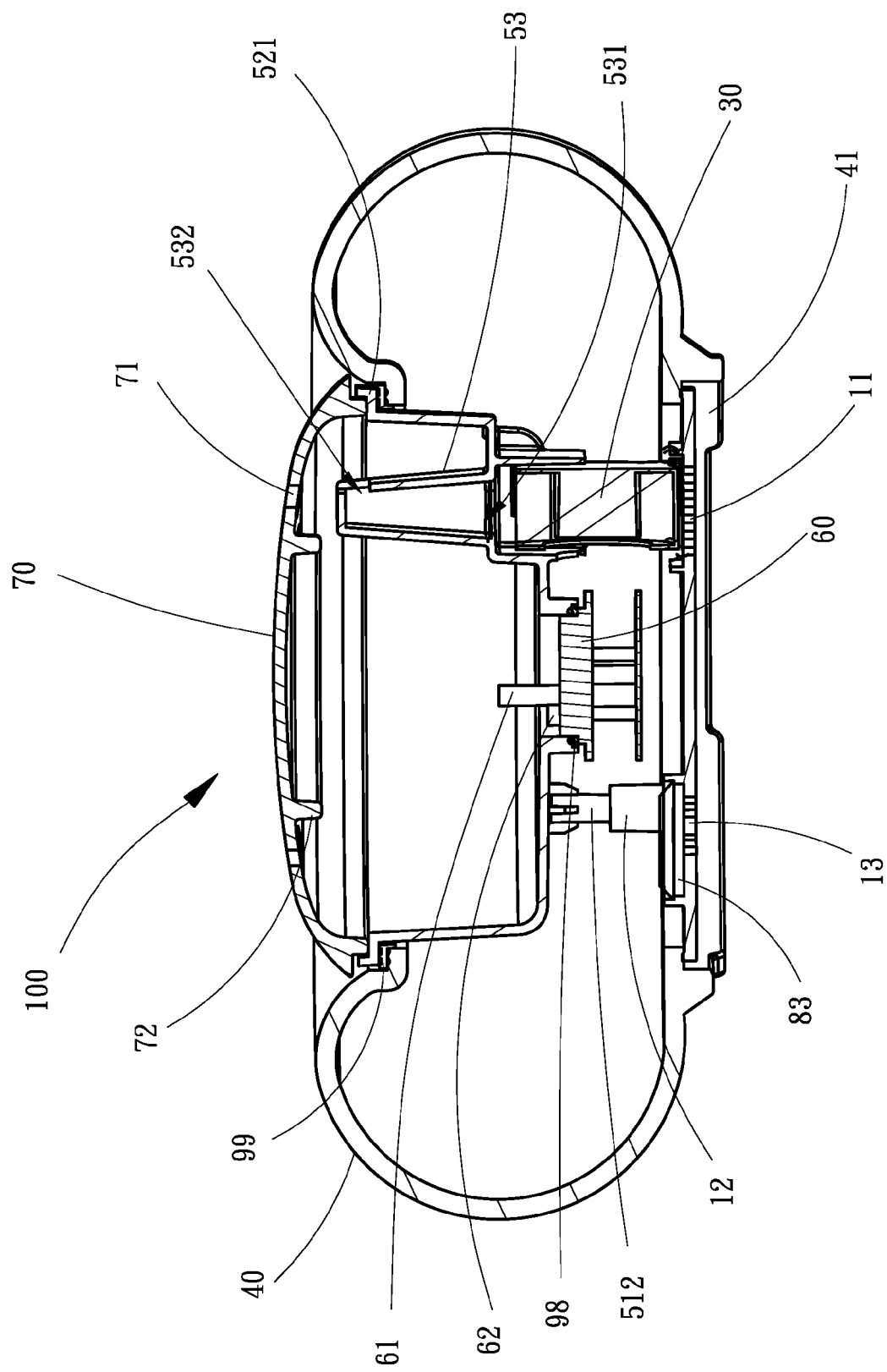
FIG. 5 is a sectional assembly view of the aromatic nebulizing diffuser in accordance with the present invention.

Referring to FIG. 5 and FIGS. 3 and 4 again, the electric fan 30 is mounted on the base panel 10 corresponding to the air vents 11 and electrically connected with the power adapter 20 to obtain the necessary working voltage for drawing in outside fresh air through the air vents 11.

Referring to FIGS. 1~5 again, the shell 40 is a hollow barrel shaped like a donut that can be positioned on a flat surface stably after having the fluid container 50 held therein. The shell 40 has a plurality of foot members 41 for positioning on a flat surface (for example, the floor in a house).

Referring to FIGS. 3~5. again, the fluid container 50 comprises a horizontal bottom wall 51, a vertical peripheral wall 52 upwardly extended from the border of the horizontal bottom wall 51, a fluid chamber 54 surrounded by the horizontal bottom wall 51 and the vertical peripheral wall 52, an air conduit 53 suspending in the fluid chamber 54 and a mounting hole 511 cut through the horizontal bottom wall 51 at the center. The air conduit 53 has its one end, namely, the bottom end downwardly extending out of the horizontal bottom wall 51 and terminating in an air inlet 531 and its other end, namely, the top end suspending in the fluid chamber 54 and terminating in an air outlet 532. The fluid container 50 is accommodated inside the shell 40. The fluid container 50, the base panel 10 and the shell 40 are fastened together, keeping the air inlet 531 of the air conduit 53 in alignment with the electric fan 30.

Referring to FIGS. 3~5, the oscillator 60 according to the present invention is an ultrasonic oscillator mounted in the mounting hole 511 of the horizontal bottom wall 51 of the fluid container 50 and electrically connected to the power adapter 20 to obtain the necessary working voltage from the power adapter 20.

Referring to FIGS. 1~5, the top cover 70 is covered on the top open side of the shell 40 and forced into engagement with the rim of the fluid container 50, having a plurality of jet holes 71 cut through the top and bottom wall thereof and arranged in a circle and an annular bottom flange 72 protruded from the bottom wall corresponding to the mounting hole 511 of the fluid container 50. Further, the jet holes 71 are arranged around the annular bottom flange 72.

After understanding of the structural details of the component parts of the detachable aromatic nebulizing diffuser 100 and their arrangement, the operation of the detachable aromatic nebulizing diffuser 100 is described hereinafter.

At first, an aromatic fluid (essential oil and water mixture) is filled in the fluid chamber 54 of the fluid container 50, and then the ultrasonic oscillator 60 is turned on to oscillate the aromatic fluid into a fine mist of aromatic fluid droplets. At the same time, the electric fan 30 is started to draw in outside fresh air through the air vents 11 on the base panel 10. The intake currents of air are guided through the air inlet 531 and air outlet 532 of the air conduit 53 into the fluid chamber 54 to further carry the generated fine mist of aromatic fluid droplets out of the top cover 70 into the outside open air via the jet holes 71. Because the generated fine mist of aromatic fluid droplets is quickly carried by the induced currents of air out of the top cover 70 into the outside open air via the jet holes 71, the generated fine mist of aromatic fluid droplets will not be condensed into fluid in the jet holes 71.

Further, the annular bottom flange 72 projects into the inside of the fluid container 50 to prevent splashing of the oscillated aromatic fluid without hindering flowing of the induced currents of air with the generated fine mist of aromatic fluid droplets toward the jet holes 71. Therefore, the invention achieves better atomization of the aromatic fluid when compared to conventional designs that use an ultrasonic oscillator of the same capacity and oscillation frequency.

Further, the shell 40 can be prepared from ceramics and coated with a layer of color coating, showing the shape of a donut and providing a decorative effect.

Further, the base panel 10 has a plurality of tubular upright posts 12 perpendicularly upwardly extended from the top wall thereof. Further, the fluid container 50 has a plurality of bottom mounting rods 512 perpendicularly downwardly extended from the horizontal bottom wall 51 and respectively detachably plugged into the tubular upright posts 12 of the base panel 10. Subject to the matching design between the tubular upright posts 12 of the base panel 10 and the bottom mounting rods 612 of the fluid container 50, the fluid container 50 can be easily detachably installed, facilitating cleaning.

Referring to FIG. 5 again, by means of positioning the foot members 41 of the shell 40 on the floor, the base panel 10 is kept above the floor at a certain elevation, facilitating the operation of the electric fan 30 to draw in air through the air vents 11 and to accelerate the atomization of the aromatic fluid.

Referring to FIG. 2 again, the shell 40 has a notch 42 for accommodating a part of the power adapter 20 for easy connection of an external power cable to the power adapter 20.

Referring to FIGS. 3~5 again, the air conduit 52 has a diameter reduces gradually from the air inlet 531 toward the air outlet 532. Therefore, the air pressure of the intake flow of air increases gradually when it is flowing through the air duct 53 into the fluid chamber 54. Therefore, the produced fine mist of aromatic fluid droplets can be carried out of the fluid container 50 to the outside open air through the jet holes 71 of the top cover 70 rapidly. Further, the fluid container 50 has a top flange 521 at the top side of the peripheral wall 52. A rubber water seal 99 is mounted around the peripheral wall 52 of the fluid container 50 and stopped between the top flange 521 of the fluid container 50 and the top edge of the shell 40 to prevent leakage.

Referring to FIGS. 3~5 again, the ultrasonic oscillator 60 has a control circuit built therein that oscillates ultrasonic waves having a frequency higher than several million cycles per second. The ultrasonic oscillator 60 is mounted in the mounting hole 511 of the horizontal bottom wall 51 of the fluid container 50 and sealed with a rubber water seal 98.

Referring to FIGS. 3~5 again, the ultrasonic oscillator 60 carries a water lever sensor 61 and a light source 62. The water level sensor 61 is disposed in the fluid chamber 54 to detect the level of the contained aromatic fluid. The light source 62 is controllable to emit light, thereby illuminating the fluid chamber 54. The internal control circuit of the ultrasonic oscillator 60 controls the operation of the ultrasonic oscillator 60, the water lever sensor 61 and a light source 62. When the level of the aromatic fluid in the fluid chamber 54 is below a predetermined value, the control circuit of the ultrasonic oscillator 60 cuts off power supply from the ultrasonic oscillator 60, preventing damage. Further, the light source 62 can be comprised of at least one red LED component, at least one blue LED component, and/or at least one green LED component, or at least one multi-color LED component that emits red, blue and green light. Subject to the control of the internal control circuit of the ultrasonic oscillator 60, the light source 62 emits light of mixed color onto top cover 70. Further, the top cover 70 can be made of any of light transmissive ceramics, glass, frosted glass, plastics, acrylic, or any of a variety of transparent or translucent materials that allow light to pass through.

Referring to FIGS. 2~4, the detachable aromatic nebulizing diffuser 100 further comprises an audio source input connector 81, a music control circuit board 82 and a speaker 83. As illustrated, the audio source input connector 81 is mounted on the base panel 10 for the connection of an external sound source, for example, a music player or multimedia storage device (not shown) for sound source input. The music control circuit board 82 is mounted on the base panel 10 and electrically connected with the power adapter 20 and the music control circuit board 82, having storage means for storing natural voices, music files, animal sounds. The speaker 83 is mounted on a slotted speaker mounting zone 13 of the base panel 10 and electrically connected to the audio source input connector 81 and the music control circuit board 82 to convert an electrical signal from the audio source input connector 81 or the music control circuit board 82 into sound that is driven out of the detachable aromatic nebulizing diffuser 100 through the open spaces in the slotted speaker mounting zone 13 of the base panel 10. Therefore, sound and lighting effects are created during operation of the detachable aromatic nebulizing diffuser 100. Further, the shell 40 shields the speaker 80, the electric fan 30 and the music control circuit board 82, allowing the audio source input connector 81 to communicate with external sound source means through the notch 42 of the shell 40.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. An aromatic nebulizing diffuser, comprising:
  a base panel, said base panel having a plurality of air vents cut through top and bottom sides thereof;
  an electric fan mounted on said base panel corresponding said air vents for drawing in air;
  a fluid container, said fluid container comprising a horizontal bottom wall, a mounting through hole cut through said horizontal bottom wall; a vertical peripheral wall upwardly extended from the border of said horizontal bottom wall, a fluid chamber surrounded by said horizontal bottom wall and said vertical peripheral wall and holding an aromatic fluid, an air conduit suspending in said fluid chamber, said air conduit having a bottom air inlet extending out of said horizontal bottom wall for guiding in currents of air from said electric fan and a top air outlet for suspending above the fluid level of said aromatic fluid;
  an ultrasonic oscillator mounted in said mounting through hole of said fluid container and controllable to produce oscillating waves for causing atomization of said aromatic fluid;
  a power adapter mounted on said base panel and electrically connected with said electric fan and said ultrasonic oscillator to provide said electric fan and said ultrasonic oscillator with the necessary working voltage;
  a shell surrounding said fluid container, said shell having a top open side connected with said fluid container and a bottom open side connected with said base panel; and
  a top cover covered on said shell to close said fluid container, said top cover comprising a plurality of jet holes cut through top and bottom walls thereof in communication with the inside space of said fluid chamber and arranged in a circle and an annular bottom flange protruded from the bottom wall thereof and suspending in a top side inside said fluid chamber of said fluid container for baffling water.

2. The aromatic nebulizing diffuser as claimed in claim 1, wherein a speaker, a music control circuit board and an audio source input connector are mounted on said base panel, said speaker being electrically connected with said music control circuit board and said audio source input connector, said audio source input connector being electrically connected to said music control circuit board; said base panel comprises a slotted speaker mounting zone for the mounting of said speaker; said shell has a notch in the periphery thereof for accommodating a part of said power adapter and a part of said audio source input connector.

3. The aromatic nebulizing diffuser as claimed in claim 1, wherein said shell comprises a plurality of foot members for positioning on the floor to keep said base panel above the floor.

4. The aromatic nebulizing diffuser as claimed in claim 1, wherein said base panel comprises a plurality of tubular upright posts upwardly extended from the top wall thereof; said fluid container comprises a plurality of bottom mounting rods perpendicularly downwardly extended from the horizontal bottom wall thereof and respectively detachably plugged into the tubular upright posts of said base panel.

5. The aromatic nebulizing diffuser as claimed in claim 1, wherein said air conduit has a diameter reducing in direction from the bottom air inlet toward the top air outlet thereof.

6. The aromatic nebulizing diffuser as claimed in claim 1, wherein said shell admits light.

7. The aromatic nebulizing diffuser as claimed in claim 1, wherein said fluid container comprises a top flange and a rubber water seal mounted around the periphery thereof and stopped between said top flange and the top open side of said shell; said ultrasonic oscillator is mounted in the mounting through hole of the horizontal bottom wall of said fluid container and sealed with a rubber water seal.

8. The aromatic nebulizing diffuser as claimed in claim 1, further comprising a water lever sensor and a light source carried on said ultrasonic oscillator, said water level sensor being adapted to detect the level of the aromatic fluid in said fluid chamber, said light source being controllable by said ultrasonic oscillator to emit light in illuminating said fluid chamber.

9. The aromatic nebulizing diffuser as claimed in claim 8, wherein said light source comprises at least one red LED component, at least one blue LED component, and/or at least one green LED component, or at least one multi-color LED component that emits light of mixed color.

* * * * *